Figure 1:
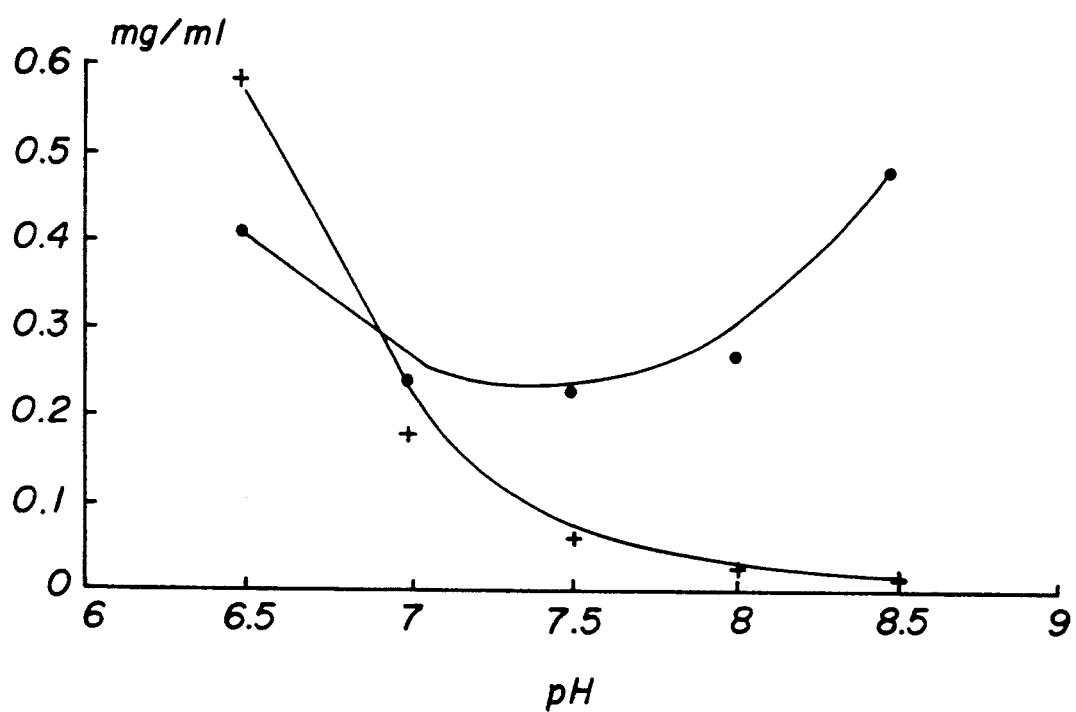

United States Patent [19]

Rozier

[11] Patent Number: 5,304,559
[45] Date of Patent: Apr. 19, 1994

[54] COMPOSITIONS CONTAINING A 4-QUINOLONE DERIVATIVE COMPLEXED WITH A DIVALENT METAL ION

[75] Inventor: Annouk Rozier, Clermont-Ferrand, France

[73] Assignee: Laboratoires Merck Sharp & Dohme Chibret, Paris, France

[21] Appl. No.: 742,989

[22] Filed: Aug. 9, 1991

[30] Foreign Application Priority Data

Aug. 10, 1990 [FR] France ................... 90 10254

[51] Int. Cl.⁵ .................. A61K 31/495; A61K 31/50; A61K 31/445
[52] U.S. Cl. .................... 514/255; 514/250; 514/316; 514/320; 514/321; 514/912; 514/913
[58] Field of Search ............ 514/54, 912, 913, 915, 514/944, 316, 320, 321, 255, 252

[56] References Cited

U.S. PATENT DOCUMENTS 4,861,760  8/1989  Mazuel et al. ................. 514/54

FOREIGN PATENT DOCUMENTS 0049593  9/1981  European Pat. Off. .
0142426  5/1985  European Pat. Off. .
0337231  10/1989  European Pat. Off. .
2146373  3/1973  France .
1-085459  4/1989  Japan .

OTHER PUBLICATIONS

Nakano et al., Chem. Pharm. Bull. 26(5) 1505-1510 (1978).

Primary Examiner—Zohreh A. Fay
Attorney, Agent, or Firm—Sylvia A. Ayler; Mark R. Daniel; Joseph F. DiPrima

[57] ABSTRACT

The present invention concerns a fluid pharmaceutical composition intended to be brought into contact with a physiological fluid, characterized in that it contains, as active principle, at least one 4-quinolone derivative complexed with a divalent metal ion selected from $Cu^{++}$, $Zn^{++}$ and $Mg^{++}$, the said complex being in the form of particles of a size compatible with parenteral or ophthalmic administration, in suspension in a fluid dispersant and not being subject to a crystalline growth phenomenon during storage of the said composition; the invention also provides a process for preparing a pharmaceutical composition of this type.

10 Claims, 1 Drawing Sheet

5,304,559

COMPOSITIONS CONTAINING A 4-QUINOLONE DERIVATIVE COMPLEXED WITH A DIVALENT METAL ION

The present invention relates to a fluid pharmaceutical composition containing, as active principle, at least one 4-quinolone derivative complexed to a divalent metal ion.

4-Quinolone derivatives are well known for their inhibitory activity on the synthesis of bacterial deoxyribonucleic acid, and consequently are good bactericides. Amongst these compounds those which may be mentioned in particular are nalidixic, oxolinic and pipemidic acids, cinoxacin, flumequine and norfloxacin.

However, some of these antibacterial compounds have, at neutral pH, insufficient solubility to afford concentrated solutions.

The formulation of these compounds in suspension form gives rise to a problem associated with their residual solubility. Thus, crystal growth occurs, leading to non-resuspendability in the case of these particular compounds. This phenomenon is observed during storage of the suspension by the manifestation of a sediment at the bottom of the container, which is particularly prejudicial for parenteral or ophthalmic formulations.

The object of the present invention is to provide a fluid pharmaceutical composition based on at least one 4-quinolone derivative and formulated in such a way that the phenomenon of growth of crystals customarily observed during storage of suspensions of these derivatives is overcome.

More precisely, the present invention relates to a fluid pharmaceutical composition intended to be brought into contact with a physiological fluid, characterized in that it contains, as active principle, at least one 4-quinolone derivative complexed with a divalent metal ion selected from $Cu^{++}$, $Zn^{++}$ and $Mg^{++}$, the said complex being in the form of particles of a size compatible with parenteral or ophthalmic administration, in suspension in a fluid dispersant and not being subject to a phenomenon of growth of crystals during storage of said composition.

The present invention thus demonstrates that it is possible to use, as active principle in fluid pharmaceutical compositions, 4-quinolone derivatives stabilized in the form of a complex with one of the above-mentioned divalent metal ions.

To this end, the chosen 4-quinolone derivative is converted to a 4-quinolone/divalent metal ion complex and the particles of the complex formed are dispersed in a fluid dispersant. The residual solubility of the 4-quinolone derivative thereby complexed is thence sufficiently reduced to be free of the usually observed phenomenon of growth of crystals.

These particles suitably have a size smaller than about 25 μm, and preferably smaller than about 10 μm. These particles therefore have the advantage of possessing a size compatible with ophthalmic or parenteral use and, moreover, are stable in aqueous medium at neutral pH.

In a preferred embodiment, the compositions according to the invention are ophthalmic compositions.

Recently, pharmaceutical compositions have been proposed which, in contact with a physiological fluid, undergo a liquid/gel phase transition (see EP-A-0227494). In the compositions described therein, polysaccharide derivatives which, under the effect of an increase in the ionic force, give a gel in situ, are used as fluid dispersant.

This type of pharmaceutical composition, based on a dispersant showing liquid/gel phase transition, is of obvious interest in comparison with pre-existing formulations. Thus, owing to their fluid form, these compositions permit easy administration of the active principle which they contain. Moreover, the liquid/gel phase transition nature of the dispersant used enables the activity of the active principle contained in these compositions to be prolonged.

In particular, in the treatment of ophthalmic disorders, this type of composition enables the drawbacks encountered with the standard formulations to be overcome.

In a preferred embodiment, therefore, the dispersant used in the composition according to the invention is a medium which undergoes a liquid/gel phase transition in contact with a physiological fluid.

The fluid pharmaceutical composition according to the invention so adapted therefore has the advantage, in addition to permitting the administration of 4-quinolone derivatives in a form compatible with physiological pH, of prolonging the therapeutic action of these derivatives at their sites of administration.

Thus, according to the invention, an extra-cellular anionic heteropolysaccharide produced by the bacterium *Pseudomonas elodea* and known as gellan gum is preferably used as the fluid dispersant. More particularly, the product sold under the trade name Gelrite, which is a clarified grade of gellan gum with a low degree of acetylation (marketed by the company KELCO), is preferably used as the fluid dispersant.

In accordance with the invention, it is of course possible to use a conventional fluid dispersant, i.e. one which is not subject to a liquid/gel transition phenomenon. This could be a cellulose derivative such as HPMC, MC, CMC or HEC, or a polysaccharide such as xanthan or alginate. This list is not, however, restrictive and one skilled in the art will recognise other suitable media for use as fluid dispersants which are compatible with ophthalmic or parenteral administration.

As active principle, the 4-quinolone derivative is preferably selected from nalidixic, oxolinic and pipemidic acids, cinoxacin, flumequine and norfloxacin. According to a preferential embodiment of the invention, norfloxacin is used.

The divalent metal cation, which reacts with the 4-quinolone derivative to be complexed, is initially in the form of a, preferably inorganic, metal salt. Such salts are suitably selected from $MgCl_2$, $CuCl_2$ and $ZnCl_2$.

Of course, it is possible to incorporate a further active principle, which is suitably selected from an anti-glaucoma agent, an antibiotic and/or an antiviral agent, into the compositions according to the invention.

The pharmaceutical composition according to the invention must, moreover, meet the criterion for use in living matter. In particular, it must preferably be isotonic and have a pH of between about 6.5 and 8.5. For this reason, other compounds, such as agents rendering the composition isotonic, preservatives and buffer systems, will advantageously be incorporated. Preferably, the pH of the composition according to the invention will be between about 8.0 and 8.5.

The divalent metal cation/4-quinolone derivative complex is preferably formed using at least one equivalent of the divalent metal cation per two equivalents of the chosen 4-quinolone derivative. However, except where the composition contains viscosity/gelification agents such as gellan gum (e.g. Gelrite), xanthan and alginate, which gel in the presence of certain cations, it is possible to use an excess of the divalent metal cation.

The fluid pharmaceutical compositions according to the invention have several advantages.

Firstly, they permit formulations based on 4-quinolone derivatives to be produced at neutral pH, in the form of stable suspensions. These suspensions can therefore be stored for prolonged time without the risk of crystalline growth, and remain compatible with parenteral or ophthalmic use.

Moreover, by virtue of the simultaneous use of a fluid dispersant exhibiting phase transition they enable a prolonged effect of the 4-quinolone derivative dispersed in the said medium to be ensured. This has the advantage for the patient of reducing the number of times the medicament has to be taken, whilst ensuring effective action of the said active principle.

The present invention also provides a process for the preparation of a composition according to the invention. More particularly, this process comprises the following steps:

(a) preparation of a solution A of a 4-quinolone/divalent metal ion complex by mixing the two components in a stoichiometric ratio of two equivalents of 4-quinolone derivative per at least one equivalent of divalent metal ion, in acid solution;

(b) precipitation of the complex thus obtained by rendering the said solution alkaline with an alkaline agent B;

(c) introduction of a concentrated solution of a fluid dispersant C into the mixture of A and B; and (d) recovery of the fluid composition according to the invention thereby obtained.

Since the compositions according to the invention are intended for parenteral administration or for ophthalmic application for the treatment of ophthalmic disorders, it is important to ensure that the risk of contamination is minimised. To this end, each of the three components used, i.e. the 4-quinolone/divalent metal ion complex A, the alkaline agent B and the concentrated solution of the fluid dispersant C, is sterilized beforehand.

The solutions A and B are preferably sterilized by filtration, and the concentrated solution of the fluid dispersant C by heating in an autoclave.

In the case of Gelrite, the concentrated solution of this particular fluid dispersant C is preferably introduced into the mixture of A and B in such an amount as to obtain a fluid composition according to the invention based on 0.6% of Gelrite.

As will be appreciated, it is possible to introduce excipients and/or other active principles into the solutions A and C.

The non-limiting Examples and FIG. 1 given below will enable other advantages and characteristics of the present invention to be appreciated.

FIG. 1 records the solubility of norfloxacin, with or without magnesium, as a function of the pH.

EXAMPLE 1

Norfloxacin is used as the 4-quinolone derivative, Gelrite as the fluid dispersant and magnesium chloride hexahydrate as the divalent metal ion.

Principle: The norfloxacin-magnesium complex is precipitated in an acid solution containing the two compounds by adding an alkaline agent. A concentrated solution of the fluid dispersant is then added to the suspension of the metal complex so as to obtain a final concentration of 0.6% of fluid dispersant.

Three solutions are used:

| Solution A | |
|---|---|
| anhydrous norfloxacin | 1.0 g |
| magnesium chloride hexahydrate | 0.319 g |
| N hydrochloric acid | 2.8 ml |
| benzododecinium bromide | 0.033 g |
| water for injection qs | 100.0 g |
| Solution B | |
| tromethamine | 0.5N |
| Solution C | |
| anhydrous Gelrite | 1.0 g |
| mannitol | 7.17 g |
| water for injection qs | 100.0 g |

Solutions A and B are sterilized by filtration and solution C by heating in an autoclave. Under sterile conditions, solution B is added to a sample of solution A (30 g) so as to obtain a pH value of between 8.0 and 8.5. This causes the precipitation of the norfloxacin-magnesium complex. Solution C is itself heated to 40° C. to lower its viscosity and an aliquot (60 g) of this solution C is then added to the mixture of A and B, with stirring. Water is then added to the mixture thus obtained so as to adjust the mixture to 100 g.

According to this process, the following formulation is obtained:

| Norfloxacin-magnesium suspension | |
|---|---|
| anhydrous Gelrite | 0.600 g |
| anhydrous norfloxacin | 0.300 g |
| magnesium chloride hexahydrate | 0.096 g |
| N/10 HCl | 8.400 ml |
| tromethamine qs pH | 8.0–8.5 |
| mannitol | 4.300 g |
| benzododecinium bromide | 0.010 g |
| water for injection qs | 100.00 g |

EXAMPLE 2

Formulation examples for ophthalmic compositions of norfloxacin dispersed in Gelrite, according to the invention.

| Norfloxacin-zinc suspension | |
|---|---|
| anhydrous Gelrite | 0.600 g |
| anhydrous norfloxacin | 0.300 g |
| zinc sulphate heptahydrate | 0.135 g |
| N/10 HCl | 8.400 ml |
| tromethamine qs pH | 8.0–8.5 |
| mannitol | 4.300 g |
| benzododecinium bromide | 0.010 g |
| water for injection qs | 100.00 g |
| Norfloxacin-copper suspension | |
| anhydrous Gelrite | 0.600 g |
| anhydrous norfloxacin | 0.300 g |
| copper chloride dihydrate | 0.080 g |
| N/10 HCl | 8.400 ml |
| tromethamine qs pH | 8.0–8.5 |
| mannitol | 4.300 g |
| benzododecinium bromide | 0.010 g |
| water for injection qs | 100.00 g |

EXAMPLE 3

A study of the solubility of norfloxacin at 23° C., with or without magnesium, as a function of the pH.

This study was carried out with a pharmaceutical composition based on the norfloxacin-magnesium complex obtained according to the invention. The results are illustrated in FIG. 1 below, in which the solid circles (.) represent norfloxacin alone and the crosses (+) represent norfloxacin plus magnesium.

From FIG. 1, it emerges that, at physiological pH, norfloxacin alone has insufficient solubility to afford a solution containing the therapeutic dose, but nevertheless has too high a residual solubility to afford a stable suspension. The norfloxacin-magnesium complex, on the other hand, possesses, at physiological pH, a somewhat lower residual solubility, making it possible to obtain a stable suspension.

What is claimed is:

1. In a fluid pharmaceutical composition intended to be brought into contact with a physiological fluid, said composition containing, as active principle, a pharmaceutically effective amount of at least one 4-quinolone derivative in suspension in a fluid dispersant, the improvement wherein the 4-quinolone derivative is complexed with a divalent metal ion selected from $Cu++$, $ZN++$ and $Mg++$, said complex being in the form of particles of a size compatible with parenteral or ophthalmic administration and not being subject to a crystalline growth phenomenon during storage of the said composition.

2. A composition according to claim 1, characterized in that it is an ophthalmic composition.

3. A composition according to claim 1 wherein the particles of the 4-quinolone/divalent metal ion complex have a size smaller than about 25 μm.

4. A composition according to claim 1 wherein the fluid dispersant is a medium which undergoes a liquid/gel phase transition in contact with the physiological fluid.

5. A composition according to claim 4 wherein the dispersant is a gellan gum.

6. A composition according to claim 1 wherein the 4-quinolone derivative is selected from the group consisting of nalidixic, oxolinic and pipemidic acids, cinoxacin, flumequine and norfloxacin.

7. A composition according to claim 6 wherein the 4-quinolone derivative is norfloxacin.

8. A composition according to claim 1, characterized in that it has a pH of between 6.5 and 8.5.

9. A composition according to claim 1, characterized in that it also contains other active principles selected from antiglaucoma agents, antibiotics and antiviral agents.

10. A process for the preparation of a composition according to claim 1, which process comprises the following steps:
    (a) a solution A of a 4-quinolone/divalent metal ion complex is prepared by mixing two equivalents of 4-quinolone derivative with at least one equivalent of divalent metal ion, in acid solution;
    (b) the complex thus obtained is precipitated by rendering the solution alkaline with an alkaline agent B;
    (c) a concentrated solution of a fluid dispersant C is introduced into the mixture of A and B; and
    (d) the fluid composition thereby obtained is recovered.

* * * * *